(12) United States Patent
Maruyama

(10) Patent No.: US 12,256,977 B2
(45) Date of Patent: Mar. 25, 2025

(54) HIGH FREQUENCY VASCULAR CLOSURE DEVICE

(71) Applicant: TERUMO MEDICAL CORPORATION, Somerset, NJ (US)

(72) Inventor: Tomoji Maruyama, Bear, DE (US)

(73) Assignee: Terumo Medical Corporation, Somerset, NJ (US)

(*) Notice: Subject to any disclaimer, the term of this patent is extended or adjusted under 35 U.S.C. 154(b) by 886 days.

(21) Appl. No.: 16/595,820

(22) Filed: Oct. 8, 2019

(65) Prior Publication Data

US 2021/0100604 A1 Apr. 8, 2021

(51) Int. Cl.
*A61B 18/14* (2006.01)
*A61B 17/00* (2006.01)
*A61B 17/28* (2006.01)
*A61B 18/00* (2006.01)
*A61B 18/12* (2006.01)

(52) U.S. Cl.
CPC ...... *A61B 18/1445* (2013.01); *A61B 17/0057* (2013.01); *A61B 17/2833* (2013.01); *A61B 2017/00654* (2013.01); *A61B 2017/00778* (2013.01); *A61B 2018/00077* (2013.01); *A61B 2018/00404* (2013.01); *A61B 2018/126* (2013.01); *A61B 2018/1475* (2013.01)

(58) Field of Classification Search
CPC ............ A61B 18/1445; A61B 17/0057; A61B 17/2833; A61B 2017/00654; A61B 2017/00778; A61B 2018/00077; A61B 2018/00404; A61B 2018/126; A61B 2018/1475; A61B 2018/00273; A61B 2018/00279; A61B 2018/0063; A61B 17/2909; A61B 17/2841; A61B 2017/00628; A61B 2018/00589; A61B 2018/00595
See application file for complete search history.

(56) References Cited

U.S. PATENT DOCUMENTS

| | | | |
|---|---|---|---|
| 5,496,317 A * | 3/1996 | Goble | A61B 18/1445 600/564 |
| 5,827,271 A | 10/1998 | Buysse et al. | |
| 7,182,763 B2 | 2/2007 | Nardella | |
| 7,678,133 B2 | 3/2010 | Modesitt | |
| 8,206,415 B2 * | 6/2012 | Pedros | A61B 18/1402 606/213 |
| 8,366,706 B2 | 2/2013 | Buchbinder et al. | |
| 8,372,072 B2 | 2/2013 | Lindenbaum et al. | |
| 8,427,216 B1 | 4/2013 | Chitturi et al. | |
| 9,011,381 B2 | 4/2015 | Yamada et al. | |

(Continued)

*Primary Examiner* — Thomas A Giuliani
*Assistant Examiner* — Abigail M Ziegler
(74) *Attorney, Agent, or Firm* — Fish & Richardson P.C.

(57) ABSTRACT

A vascular closure device seals a vascular access site upon completion of a procedure wherein a blood vessel has been punctured to accommodate a guidewire, an introducer sheath, and other intravascular devices. The device uses compression and thermal heating of an area around the puncture to obtain immediate hemostasis. Electrothermal bipolar vessel sealing is preferably employed, wherein a forceps grasps and compresses tissue from opposite sides of the puncture and then applies a high-frequency alternating electric current to cause the vessel wall between the forceps to denature and seal.

20 Claims, 10 Drawing Sheets

(56) References Cited

U.S. PATENT DOCUMENTS

| | | | |
|---|---|---|---|
| 2007/0049968 A1* | 3/2007 | Sibbitt, Jr. | A61B 17/0057 606/213 |
| 2009/0149847 A1 | 6/2009 | Yadin et al. | |
| 2009/0163903 A1 | 6/2009 | Lindenbaum et al. | |
| 2010/0179588 A1* | 7/2010 | Sater | A61B 17/0057 606/213 |
| 2019/0099215 A1* | 4/2019 | Hancock | A61B 18/1815 |
| 2019/0307473 A1* | 10/2019 | Fiksen | A61B 17/2841 |

* cited by examiner

HIGH FREQUENCY VASCULAR CLOSURE DEVICE

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to vascular closure devices, and, more specifically, to sealing a vascular access site upon completion of a procedure wherein a blood vessel has been punctured to accommodate a guidewire, an introducer sheath, and other intravascular devices.

Certain medical procedures utilize the introduction of instruments and devices into a body via a blood vessel (e.g., a femoral artery or a radial artery). Examples include coronary angiography and angioplasty. The procedures involve the creation of a puncture in the blood vessel by inserting a small catheter/needle to create the puncture, followed by insertion of a plastic introducer sheath which maintains the opening during insertion of a guidewire and other devices to perform a desired diagnostic or therapeutic intervention. Upon completion of the intervention, the devices are removed and it is necessary to close the puncture site to achieve hemostasis in an effective and efficient manner.

Conventional techniques used to stop the bleeding from a puncture include external compression (e.g., manual compression for at least 10 to 15 minutes), internal compression (e.g., using an inflatable balloon), suturing, and insertion of a biodegradable plug. It would be desirable to improve patient outcomes by reducing the time required for obtaining hemostasis, alleviating any requirement for immobilizing the patient for prolonged periods, and avoiding the need to implant or leave behind any foreign substances.

SUMMARY OF THE INVENTION

The invention utilizes compression and thermal heating of an area around the puncture to obtain immediate sealing of the blood vessel. In one preferred embodiment, electrothermal bipolar vessel sealing is employed wherein a clamp or forceps grasps and compresses tissue from opposite sides of the puncture and then applies a high-frequency alternating electric current to cause the vessel wall between the forceps to denature and seal. Sealing of vessels by thermal heating has generally been used as a technique for closing the end of a severed vessel, but has not been successfully implemented for closing punctures in a vessel wall.

In one aspect of the invention, a closure device is provided for sealing a puncture in a blood vessel. The device has a housing with a distal shaft and a proximal casing oriented along a longitudinal axis, wherein the housing defines a longitudinal passage to receive a guidewire. The device has an inner housing disposed in an internal chamber of the casing, wherein the inner housing is slidable along the longitudinal axis between a distal position and a proximal position. The inner housing is biased into the distal position. A forceps is mounted at a distal end of the distal shaft comprising first and second jaws, wherein the first and second jaws are electrically conductive and are electrically insulated from each other. The first and second jaws are pivotable between an open position and a closed position for grasping the blood vessel around the puncture to be sealed. First and second electrical conductors have their distal ends connected to the first and second jaws, respectively. Their proximal ends are configured to receive a bipolar electrical current (e.g., from a high-frequency generator). A positioning wire is retained by the distal shaft. The positioning wire is selectably extendable from a retracted position contained in the distal shaft to an extended position with a distal end protruding from the distal shaft beyond the forceps. The protruding distal end is comprised of a shape memory material that reconfigures from a substantially straight shape when stored in the retracted position into a lateral profile extending transverse to the longitudinal axis when in the extended position. A positioning lever is mounted to the inner housing and coupled to the positioning wire. The positioning lever is movable between a first position that places the positioning wire in the retracted position and a second position that places the positioning wire in the extended position, wherein the positioning lever is biased to the first position. A forceps lever is mounted to the inner housing and coupled to the first and second jaws. The forceps lever is movable between a first position that places the jaws in the closed position and a second position that places the jaws in the open position, and the forceps lever is biased to the first position.

The device is positionable along the guidewire to approach the puncture. The positioning lever is movable from the first position to the second position to place the positioning wire into the lateral profile inside the blood vessel. The distal end of the positioning wire centers the puncture with respect to the forceps when the device is partially withdrawn along the guidewire. The inner housing has a first locking feature to capture the positioning lever in the second position. The forceps lever is movable from the first position to the second position to pivot the jaws into the open position spanning the puncture. The inner housing has a second locking feature to capture the forceps lever in the second position. The inner housing is movable from the distal position to the proximal position to cause the positioning wire to retract into the distal shaft and the jaws to pivot to the closed position grasping the blood vessel across the puncture so that the puncture can be closed by activating the bipolar electrical current.

DETAILED DESCRIPTION OF PREFERRED EMBODIMENTS

Figure 1:
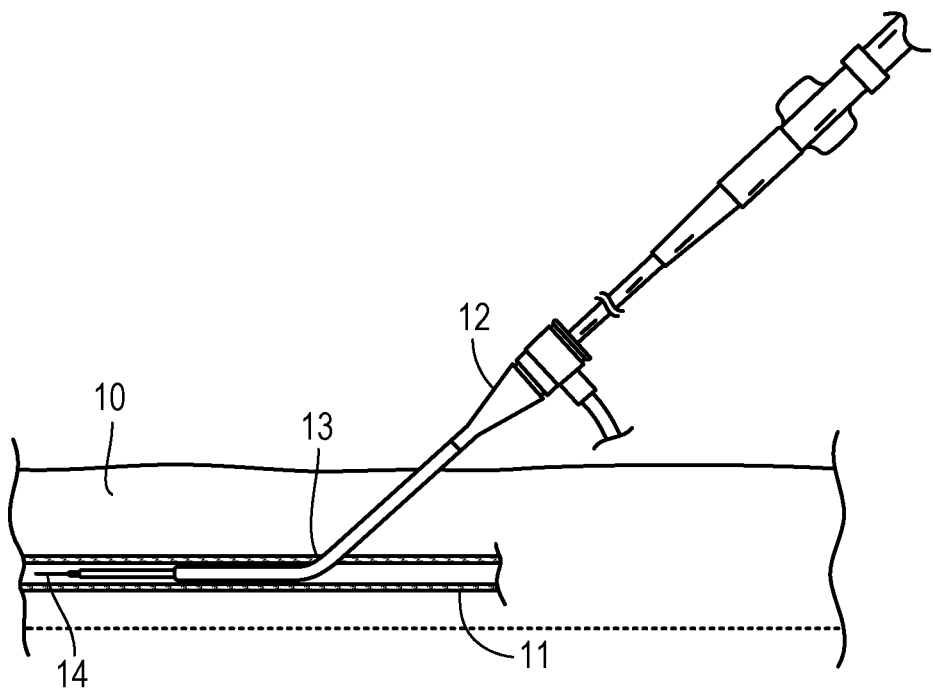
FIG. 1 is a diagram showing an interventional system introduced subcutaneously into a patient's blood vessel.
Figure 2:
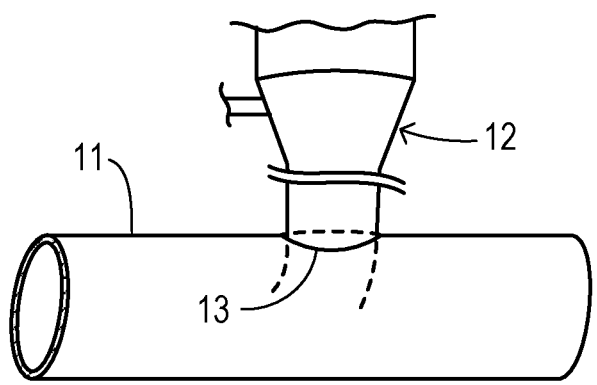
FIG. 2 is a side view showing an introducer sheath and blood vessel in greater detail.

In FIGS. 1 and 2, a body 10 of a patient contains a vessel blood vessel 11 which is punctured by an introducer sheath 12 at a puncture site 13. A guidewire 14 passes through sheath 12 and vessel 11 for guiding the introduction of various devices. Upon completion of an intervention, the devices are removed from guidewire 14 so that only guidewire 14 and sheath 12 remain. Thereafter, the tool of the present invention may be introduced over guidewire 14 to approach the puncture site 13 in order to close the blood vessel 11 as described below.

Figure 3:
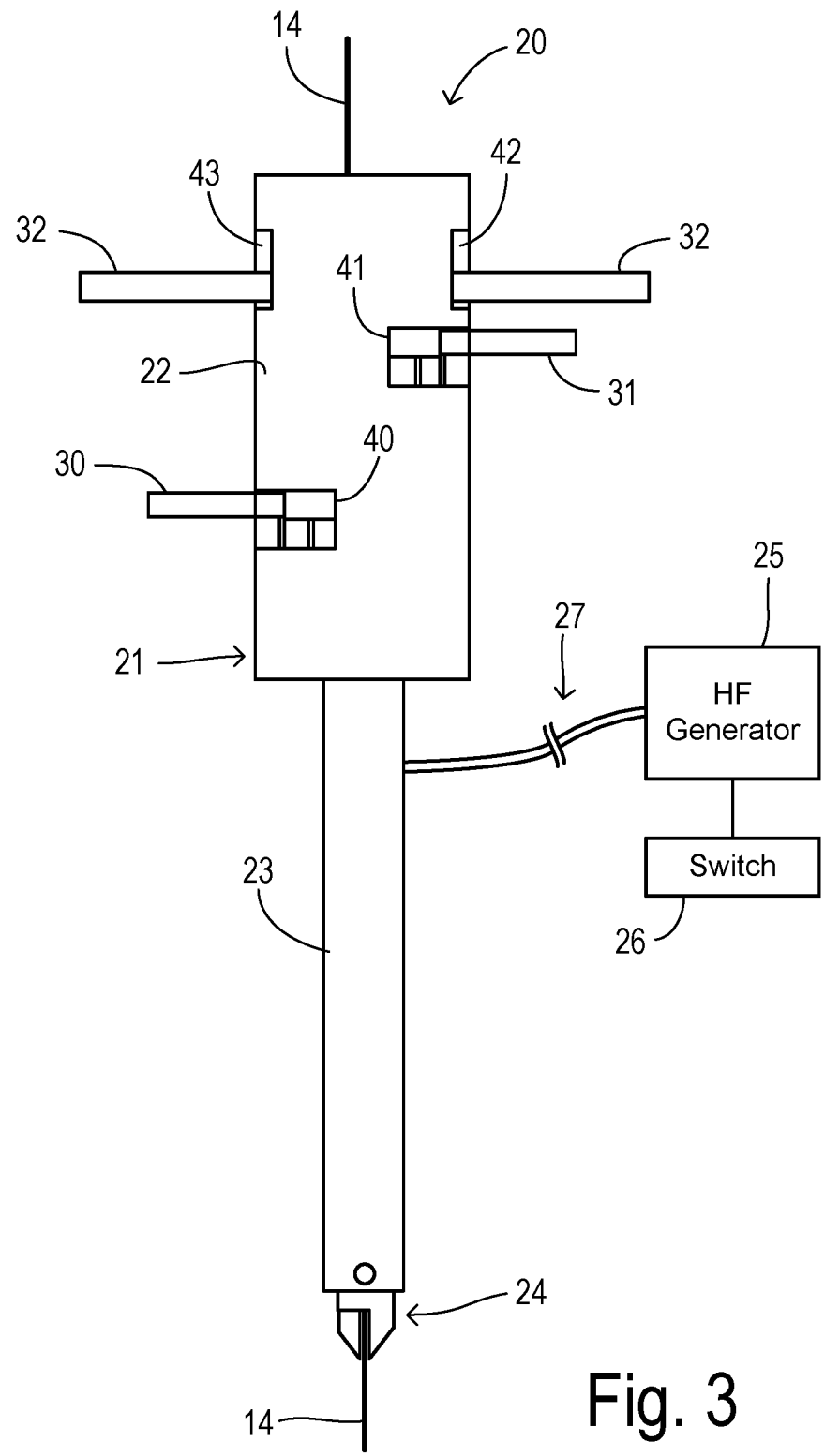
FIG. 3 is a side view of a closure device of the present invention interconnected with a bipolar power supply.

FIG. 3 shows one preferred embodiment of a closure device 20 with a longitudinal passage installed on guidewire 14. Device 20 has a housing 21 with a proximal casing 22 and a distal shaft 23 arranged along a longitudinal axis. A forceps 24 is mounted at a distal end of shaft 23 and is arranged to receive a bipolar alternating electrical current from a high-frequency (HF) generator 25 under control of a switch 26 via electrical conductors 27. Switch 26 may include a manual pushbutton or a foot pedal, for example. Generator 25 can be a type that is commercially available for performing electrothermal bipolar vessel heating. For example, generator 25 may monitor impedance during heating in order to optimize vessel sealing without charring.

Housing 21 accommodates other mechanisms described below in connection with obtaining a proper placement of device 20 and the manipulation of forceps 24. These include a first (positioning) lever 30, a second (forceps) lever 31, and a third (inner housing) lever 32, each of which is movable longitudinally to operate various portions of device 20 as explained below.

Figure 4:
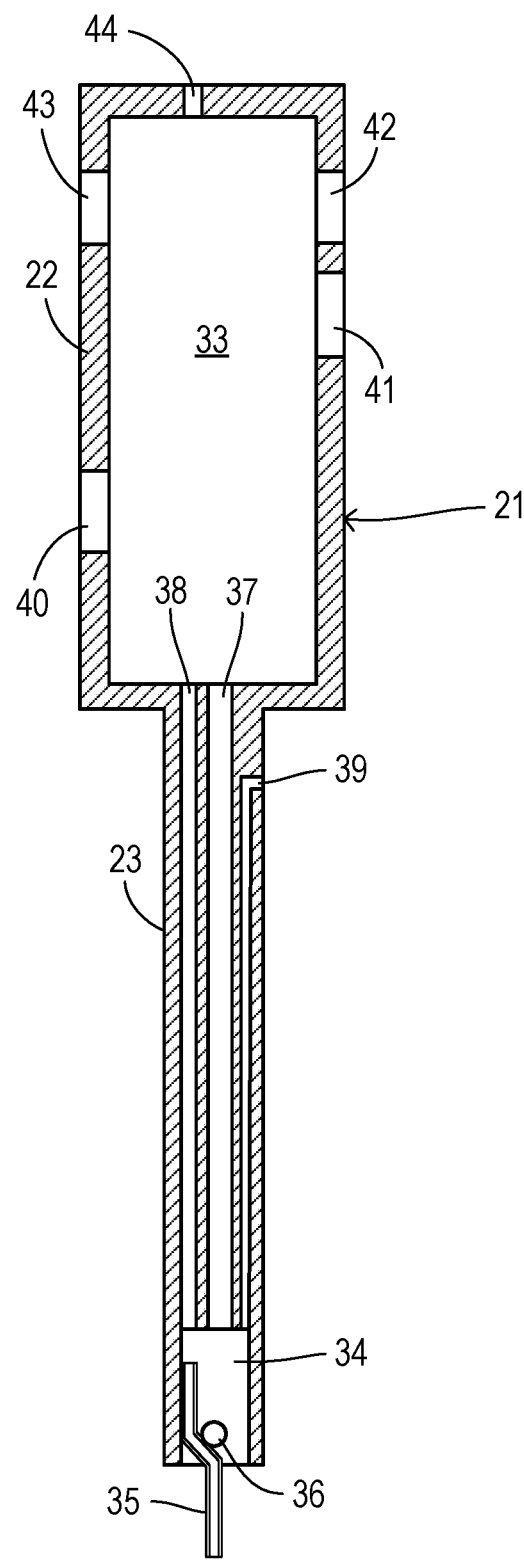
FIG. 4 is a side, cross-sectional view of an outer housing of the device of FIG. 3.

FIG. 4 shows housing 21 in cross-section to reveal an internal chamber 33 within proximal casing 22. Distal shaft 23 defines an end chamber 34 to receive forceps 24. An inner tube 35 is disposed in chamber 34 and has a distal end which is aligned with the central axis of chamber 34. An aperture 36 receives a pivot pin of forceps 24. Distal shaft 23 includes one or more passages such as passages 37, 38, and 39 to accommodate components such as an actuation pin for the forceps, a positioning wire, and electrical conductors. Instead of forming passage 38 directly within the body of shaft 23, inner tube 35 could extend the full length of distal shaft 23 (i.e., within a cylindrical bore of shaft 23). In addition, passage 39 could be combined with passage 37 (e.g., shaft 23 could provide an outer tube for carrying the actuation pin, the conductor wires, and inner tube 35, while inner tube 35 conveyed guidewire 14 and the positioning wire).

Proximal casing 22 includes side openings 40 and 41 for receiving levers 30 and 31, respectively, and side openings 42 and 43 for receiving lever 32. The levers preferably include radial handles projecting through the openings from respective internal sliding bodies. An opening 44 is provided for receiving guide wire 14.

Figure 5:
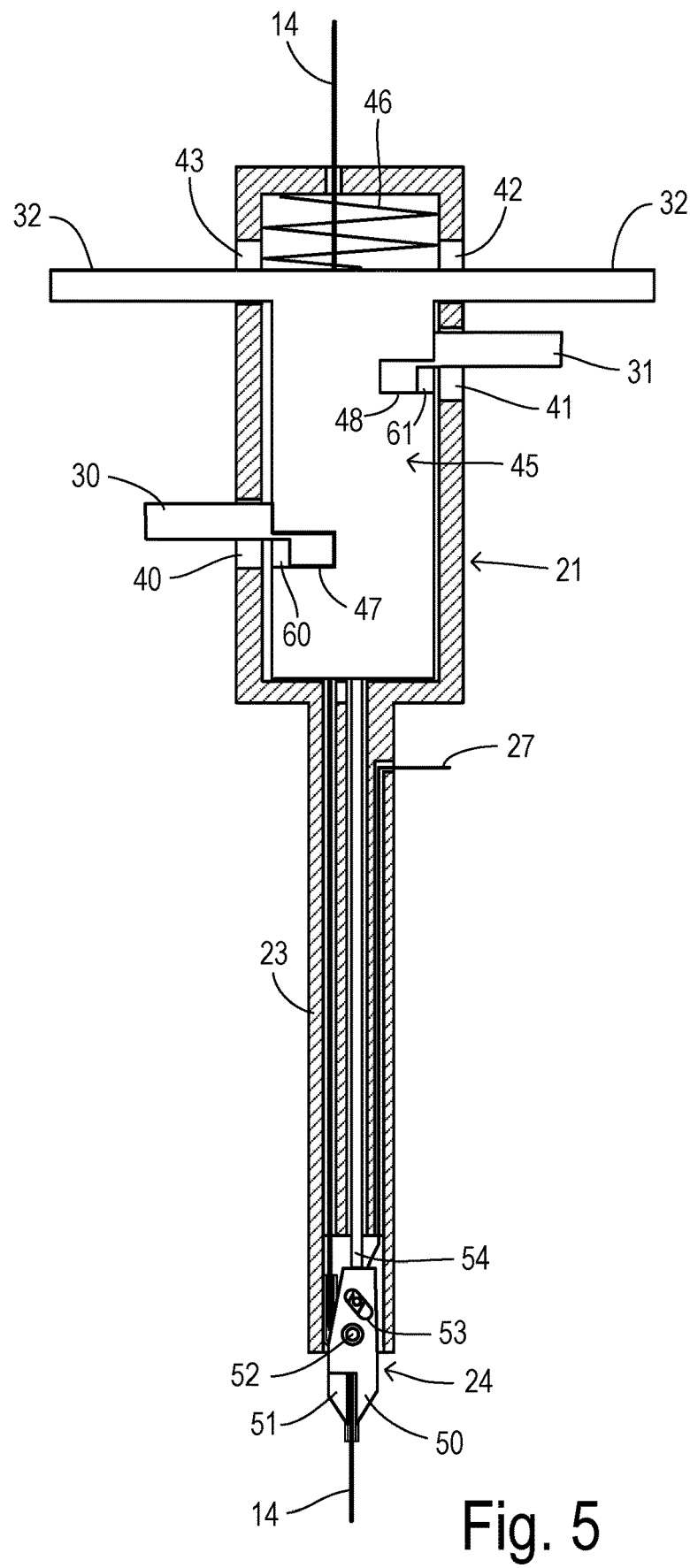
FIG. 5 is a side view of the device of FIG. 3 with the outer housing shown in cross section to reveal an inner housing and other components.
Figure 18:
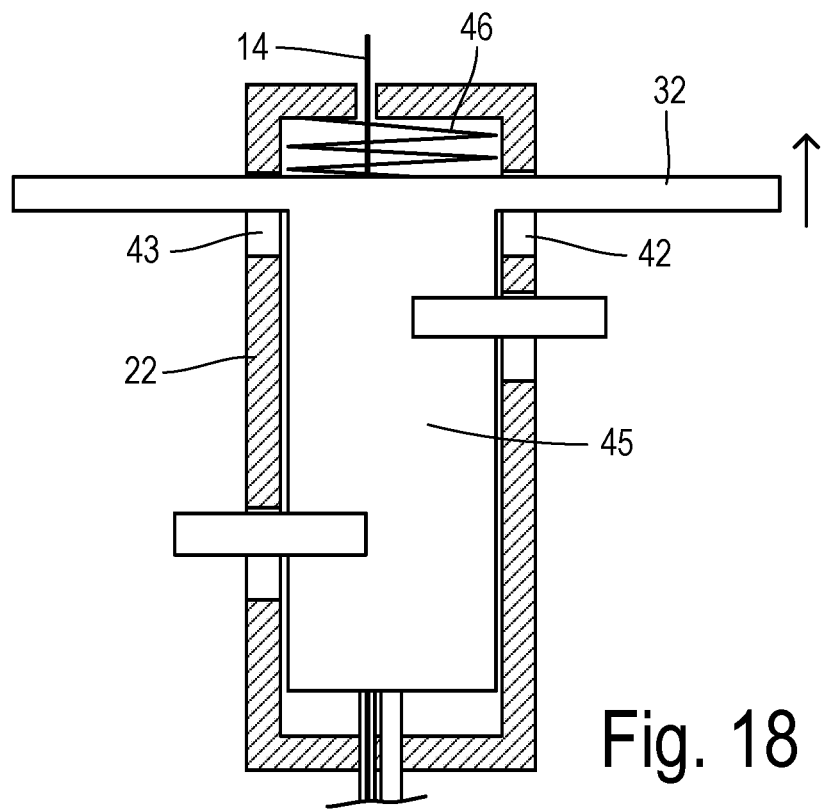
FIG. 18 is a partial cross-section of the proximal portion of the device of FIG. 3 with the outer housing shown in cross section to reveal the inner housing withdrawn to a proximal position.

FIG. 5 shows an inner housing 45 installed in internal chamber 33, wherein inner housing 45 is slidable along the longitudinal axis between a distal position as shown in FIG. 5 and a proximal position (see FIG. 18). A spring 46 biases inner housing 45 into the distal position. In the distal position, lever 32 extends from inner housing 45 and bears against distal edges of openings 42 and 43. In the proximal position, lever 32 bears against proximal edges of openings 42 and 43. Also when inner housing 45 is in the distal position, levers 30 and 31 are located at proximal edges of openings 30 and 31. Levers 30 and 31 are longitudinally movable within the inner housing 45, and can be moved in a distal direction and then rotated so that levers 30 and 31 enter locking sections 47 and 48 of corresponding openings in inner housing 45 as explained below.

Figure 17:
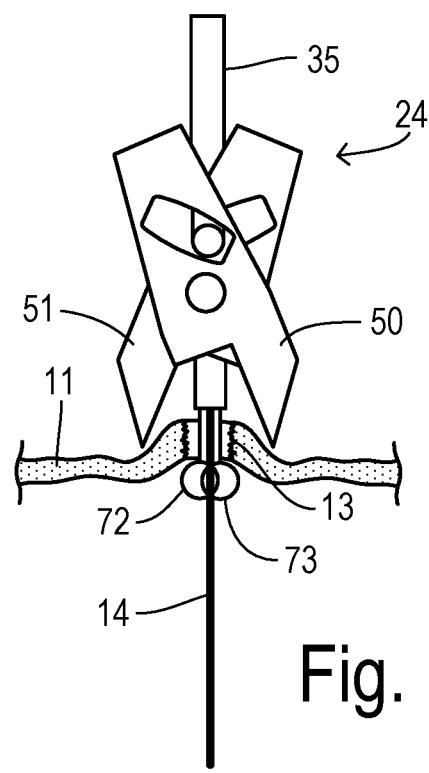
FIG. 17 shows the jaws of the forceps pivoted to the open position, ready to receive a vessel wall for compression and thermal heating.

As shown in FIG. 5, forceps 24 includes jaws 50 and 51 which are installed on a pivot pin 52 to be pivotable between a closed position as shown in FIG. 5 and an open position (see FIG. 17). Jaws 50 and 51 are electrically conductive and are connected with electrical conductors 27 in a known manner (e.g., soldering) in order to facilitate application of bipolar electrical current by jaws 50 and 51 to tissue of a vessel wall that is compressed between them. Jaws 50 and 51 are electrically insulated from each other and from the surrounding structures such as distal shaft 23 and guidewire 14 (e.g., using insulating coatings on selected surfaces). Jaw 50 includes a slanted slot 53 for receiving an end of an actuator pin 54 which is operated by lever 31, whereby longitudinal movement of pin 54 causes pivoting motion of jaw 50. Jaw 51 has a similar slot slanted in an opposite direction in order to pivot in opposition to jaw 50 (see FIG. 7).

Figure 6:
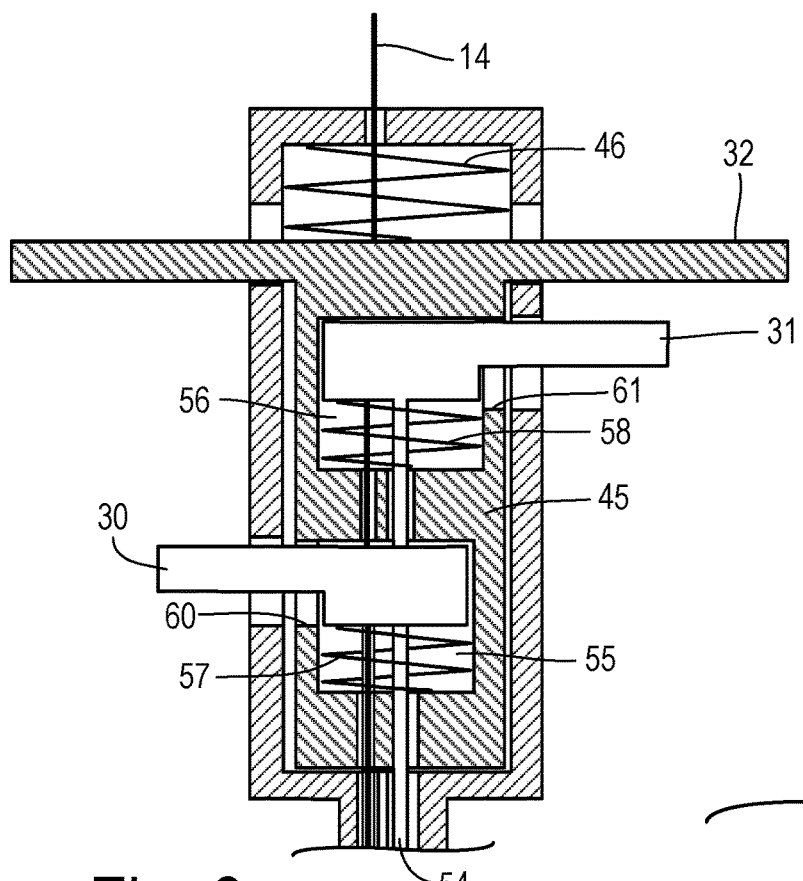
FIG. 6 is a side view of a proximal portion of the device of FIG. 3 with the outer housing and inner housing shown in cross section.

FIG. 6 shows inner housing 45 in cross-section to reveal chambers 55 and 56 which receive levers 30 and 31, respectively, in a longitudinally slidable manner. Levers 30 and 31 are biased into first (proximal) positions by springs 57 and 58. Inner housing 45 has guide slots 60 and 61 for accommodating levers 30 and 31. Guide slots 60 and 61 include locking sections 47 and 48 so that levers 30 and 31 may be manually moved to second (distal) positions against bias springs 57 and 58 in a longitudinal direction and then rotated so that levers 30 and 31 enter locking sections 47 and 48, thereby locking them at the second positions. The levers can be unlocked and returned to the biased positions by counter-rotation to exit the locking sections. Lever 30 is affixed to a positioning wire described in more detail below.

Actuator pin 54 extends from lever 31 in a continuous manner by passing through a central aperture in lever 30 (not shown). Guidewire 14 may pass along an edge of chambers 55 and 56 so as not to interfere with operation of levers 30 and 31.

Figure 7:
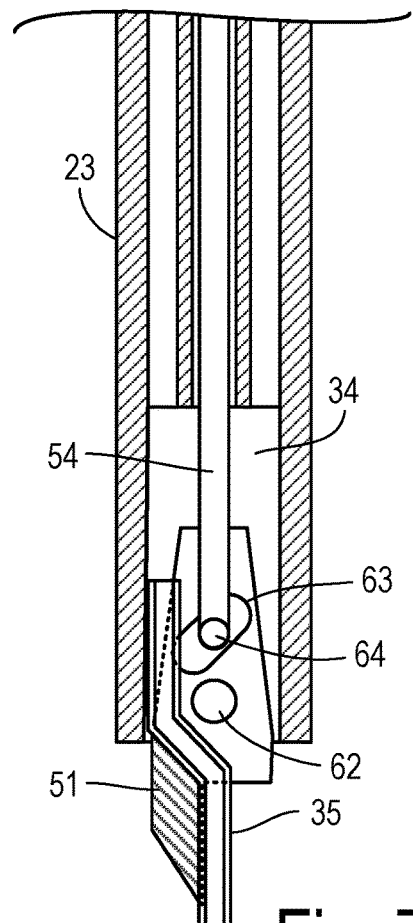
FIG. 7 is a side view of a distal portion of the device of FIG. 3 shown in partial cross section.

FIG. 7 shows the distal end of distal shaft 23 in greater detail (jaw 50 is removed). Jaw 51 includes an aperture 62 for receiving pivot pin 52 and a slanted slot 63 receiving an end of actuator pin 54. The distal end 64 of actuator pin 54 may have a "T" shape with respective crossmembers entering slanted slots 53 and 63.

Figure 8:
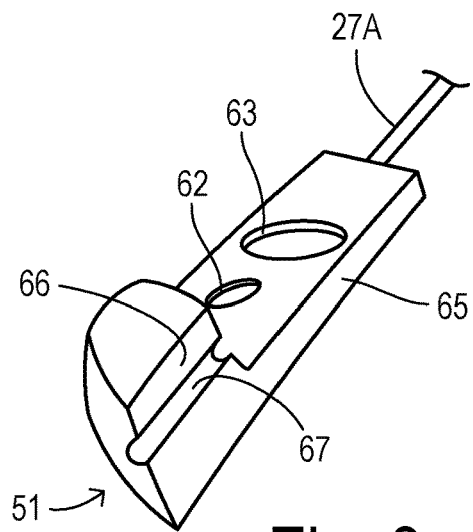
FIG. 8 is a perspective view of a jaw of the forceps of the device of FIG. 3.

Jaw 51 is shown in greater detail in FIG. 8. A main body 65 is electrically connected to a first electrical conductor 27A at a proximal end. A second conductor 27B connects to jaw 50 (not shown). A compression surface 66 is provided at the distal, inside-facing of jaw 51 for compressing tissue (i.e., the vessel wall) with a corresponding compression surface of jaw 50. One or both of the jaws further includes a groove 67 extending longitudinally for accommodating the passage of guidewire 14 and the positioning the wire to be described below.

Figure 9:
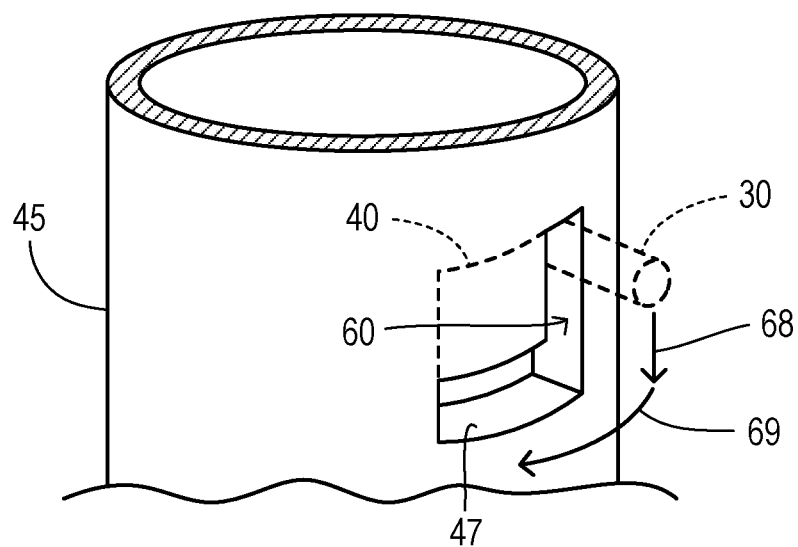
FIG. 9 is a perspective view showing a portion of the proximal portion of the device of FIG. 3 with a guide slot.

FIG. 9 shows a perspective view of a portion of inner housing 45 including opening 60 which acts as a guide slot for lever 30. Guide slot 60 has a longitudinal arm adapted to allow longitudinal movement of lever 30 and a circumferential arm which forms locking section 47. The radial handle portion of lever 30 projects radially through guide slot 60 and is movable in the longitudinal arm along a direction 68 to move lever 30 and its actuation pin from the first (proximal) position to the second (distal) position. Then lever 30 can be rotated along the circumferential arm in the direction of arrow 69 to lock lever 30 in the second position. The openings in outer housing 21 span an area to accommodate all possible movements of the levers within inner housing 45 (e.g., square profiles that expose the guide slots of inner housing 45). FIG. 9 has a dashed line to show a portion of a footprint corresponding to the position of opening 40 of outer housing 21 when projected onto inner housing 45.

Figure 10:
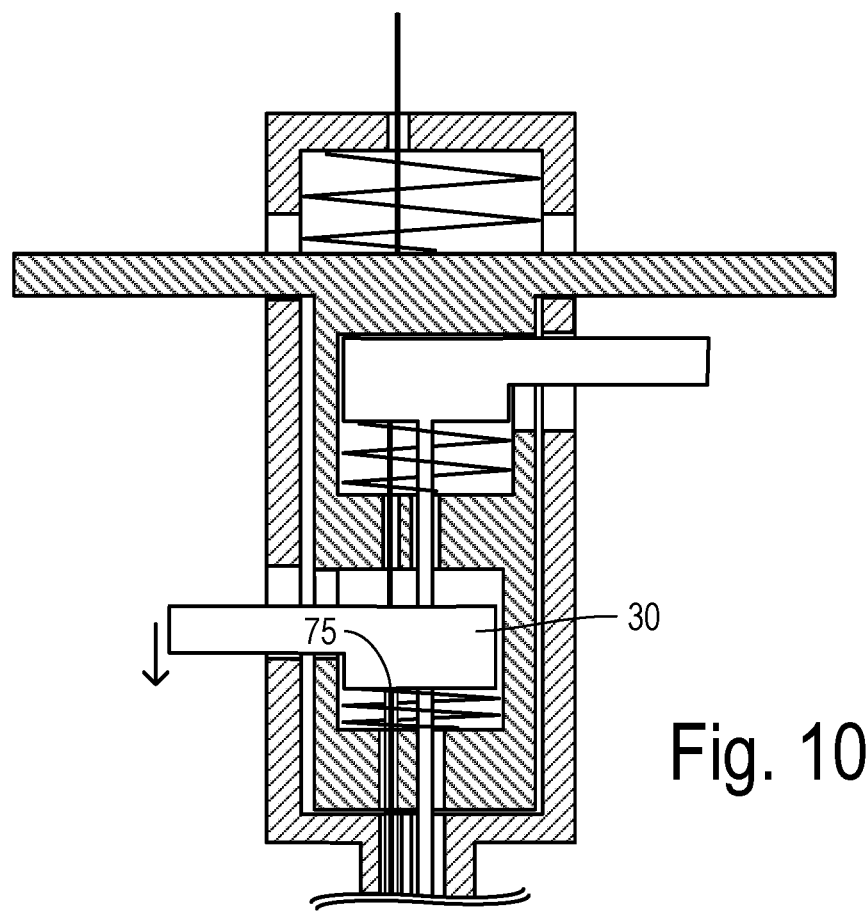
FIG. 10 is a side view of the proximal portion shown in FIG. 6 with the positioning lever moved to a second position which extends a positioning wire.
Figure 11:
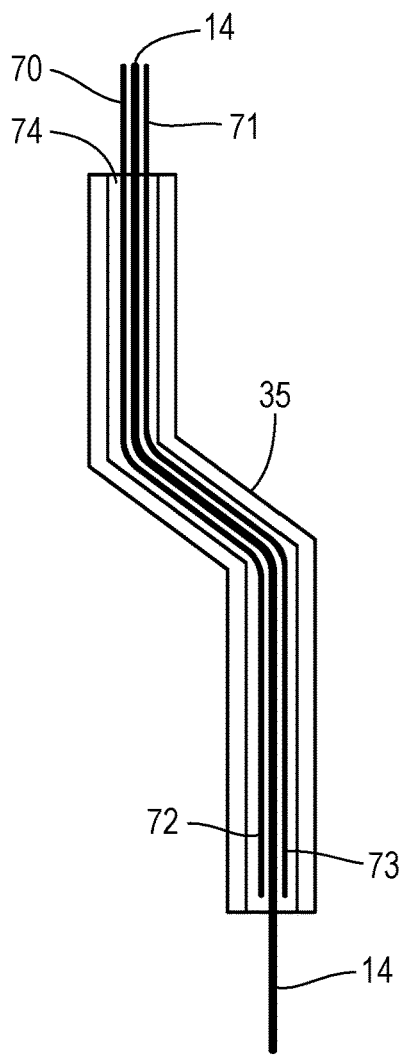
FIG. 11 shows an inner tube and a distal end of the positioning wire in a retracted position.
Figure 12:
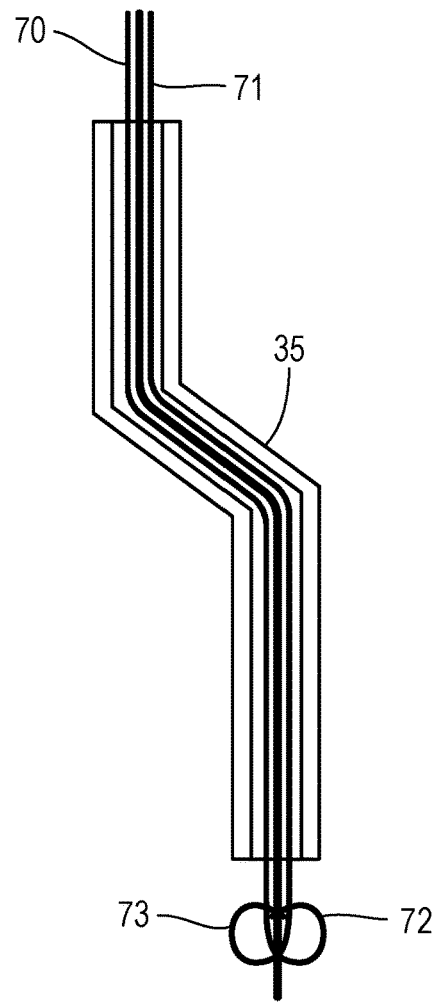
FIG. 12 shows an inner tube and a distal end of the positioning wire in an extended position.
Figure 13:
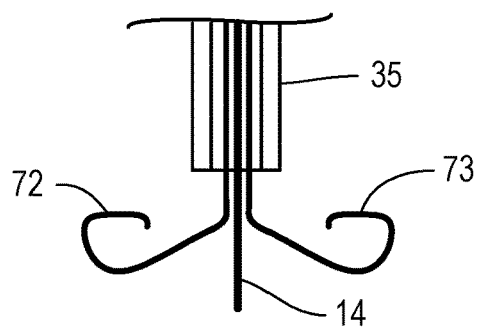
FIG. 13 shows the extended positioning wire of FIG. 12 as seen from a vantage point transverse to the vantage point of FIG. 12.

FIGS. 10-13 illustrate the positioning wire of the invention which serves to align tool 20 and puncture 13 under control of lever 30. Preferably, the positioning wire may include at least two wire members 70 and 71, each of which are fixed at their proximal ends to a bottom edge 75 of positioning lever 30. Therefore, positioning wires 70 and 71 are selectively extendable by moving positioning lever 30 to the second (distal) position as shown in FIG. 10. FIGS. 11 and 12 show positioning wires 70 and 71 passing through a lumen 74 in inner tube 35. FIG. 11 shows a retracted position with distal ends 72 and 73 of positioning wires 70 and 71, respectively, stored inside lumen 74. In this position, distal ends 72 and 73 are kept substantially straight by inner tube 35. At least at the distal ends 72 and 73, positioning wires 70 and 71 are comprised of a shape memory material such as nitinol. The shape memory material is constructed to provide an unrestrained shape that follows a lateral profile wherein positioning wires 70 and 71 extend transversely to the longitudinal axis of tool 20. In particular, distal ends 72 and 73 deploy generally at a right angle with respect to the axial direction of inner tube 35. The lateral profile of the memory shape is adapted to span a size larger than the diameter of puncture 13. Furthermore, the lateral profile is generally oblong, preferably having a maximum length perpendicular to the pivot plane of the forceps jaws and a minimum length parallel to the pivot plane. In one preferred embodiment, each positioning wire distal end 72 and 73 preferably turns sideways after extending outward from inner tube 35 and follows a quasi-spiral shape which proceeds radially outward and then bends back in to extend radially inward. This provides a bearing surface that can engage an inner surface of the wall of the blood vessel. FIGS. 12 and 13 show the extended position with distal ends 72 and 73 protruding from inner tube 35. In FIG. 12, the minimum side-to-side length of the lateral profile is seen (which coincides with the pivot plane). FIG. 13 is a view which is rotated by 90° to show the maximum side-to-side length of the lateral profile which occurs transverse to the pivot plane. Thus, the portions of positioning wire distal ends 72 and 73 that make significant contact with the vessel wall are separated from (i.e., rotated by 90° from) the contact points for the forceps jaws, which encourages the edges of the vessel wall around the puncture to bulge upward for grasping by the jaws.

Figure 14:
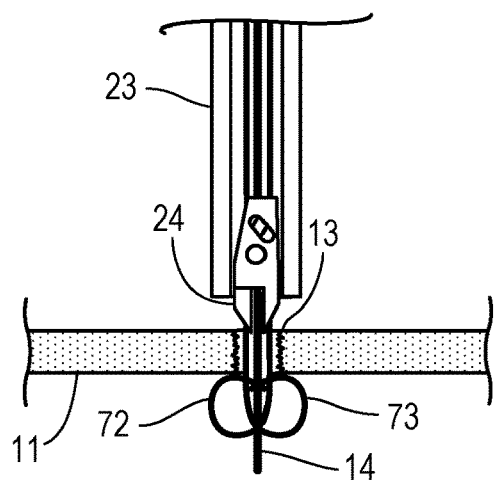
FIG. 14 is a partial cross-sectional view showing the positioning wire inside the blood vessel, wherein the cross section is taken along an axial direction of the blood vessel.
Figure 15:
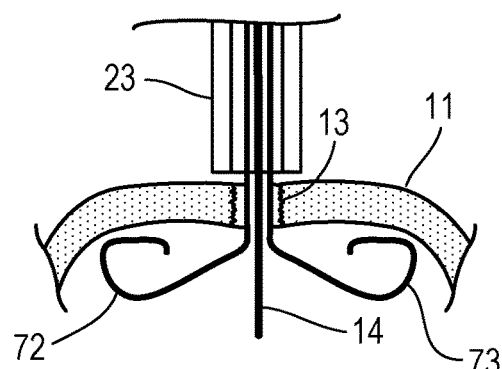
FIG. 15 is a partial cross-sectional view showing the positioning wire inside the blood vessel, wherein the cross section is taken perpendicular to the axial direction of the blood vessel.
Figure 16:
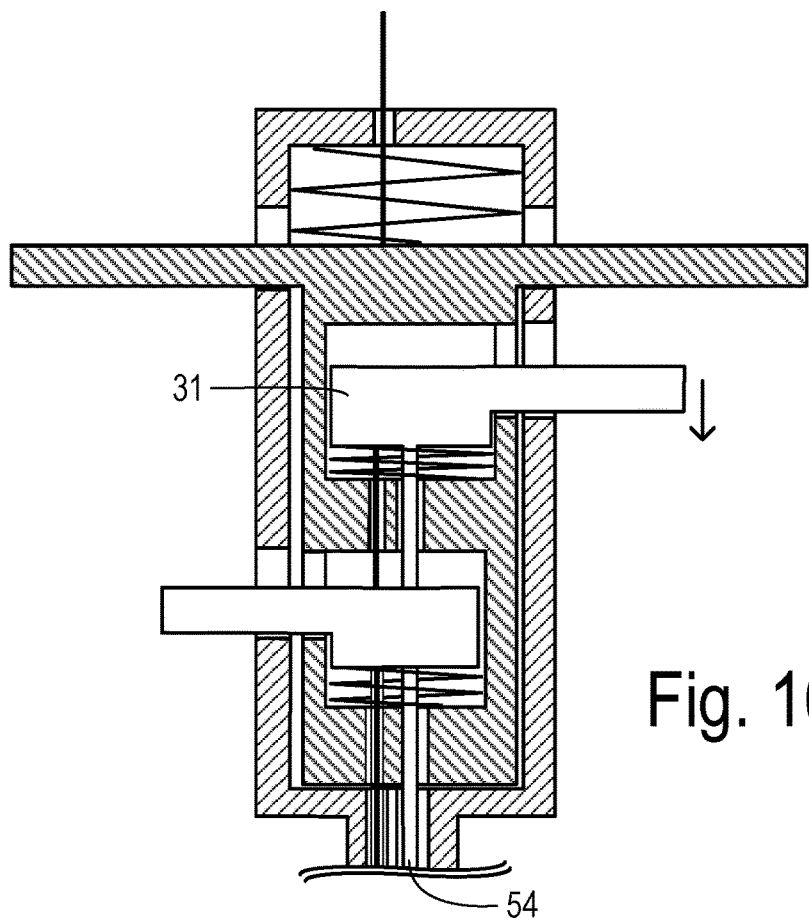
FIG. 16 is a side view of the proximal portion shown in FIG. 6 with the forceps lever moved to a second position which pivots the jaws of the forceps to an open position.

In order to align device 20 for bipolar sealing, it is advanced on guidewire 14 until its distal end approaches the puncture. Then, positioning wires 70 and 71 are extended out from inner tube 35 so that distal ends 72 and 73 deploy transversely according to the lateral profile while inside blood vessel 11 as shown in FIG. 14. FIG. 14 depicts a cross-section along the axial length of blood vessel 11. In this preferred orientation, the pivot plane of forceps 24 is arranged lengthwise along vessel 11 so that grasping of the vessel walls on opposite sides of puncture 13 pull the vessel walls longitudinally when the forceps jaws are closed. The preferred orientation is obtained when the minimum length of the lateral profile defined by distal ends 72 and 73 is arranged lengthwise in the vessel 11. FIG. 15 shows a radial cross-section of blood vessel 11 showing that the maximum length of the lateral profile is arranged perpendicular to the pivot plane (i.e., transverse to the blood flow direction) when in the preferred orientation. Furthermore, FIGS. 14 and 15 show the condition wherein device 20 has been slightly withdrawn along guidewire 14 (after extending the positioning wires) so that the deployed portions of positioning wires 72 and 73 have been pulled into contact with the vessel wall (simultaneously pulling puncture 13 into central alignment). After achieving this condition, forceps lever 31 can be deployed in a distal direction as shown in FIG. 16 and then locked in the second (distal) position. Consequently, actuation pin 54 moves in a distal direction causing jaws 50 and 51 of forceps 24 to open as depicted in FIG. 17. The interaction between forceps 24 and positioning wire distal ends 72 and 73 results in portions of the vessel wall around puncture 13 squeezing up between the opposing compression surfaces of jaws 50 and 51. In this state, inner housing 45 will then be retracted from its distal position to the proximal position as shown in FIG. 18 by pulling upward (proximally) on lever 32. Lever 32 moves upward in openings 42 and 43 while bias spring 46 is compressed. The retracting movement causes positioning wires 70 and 71 to retract into inner tube 35 and forceps jaws 50 and 51 to close. In that position, the HF generator can be activated and the puncture is closed by thermal heating. Preferably, guidewire 14 may first be withdrawn prior to activating the thermal heating.

Figure 19:
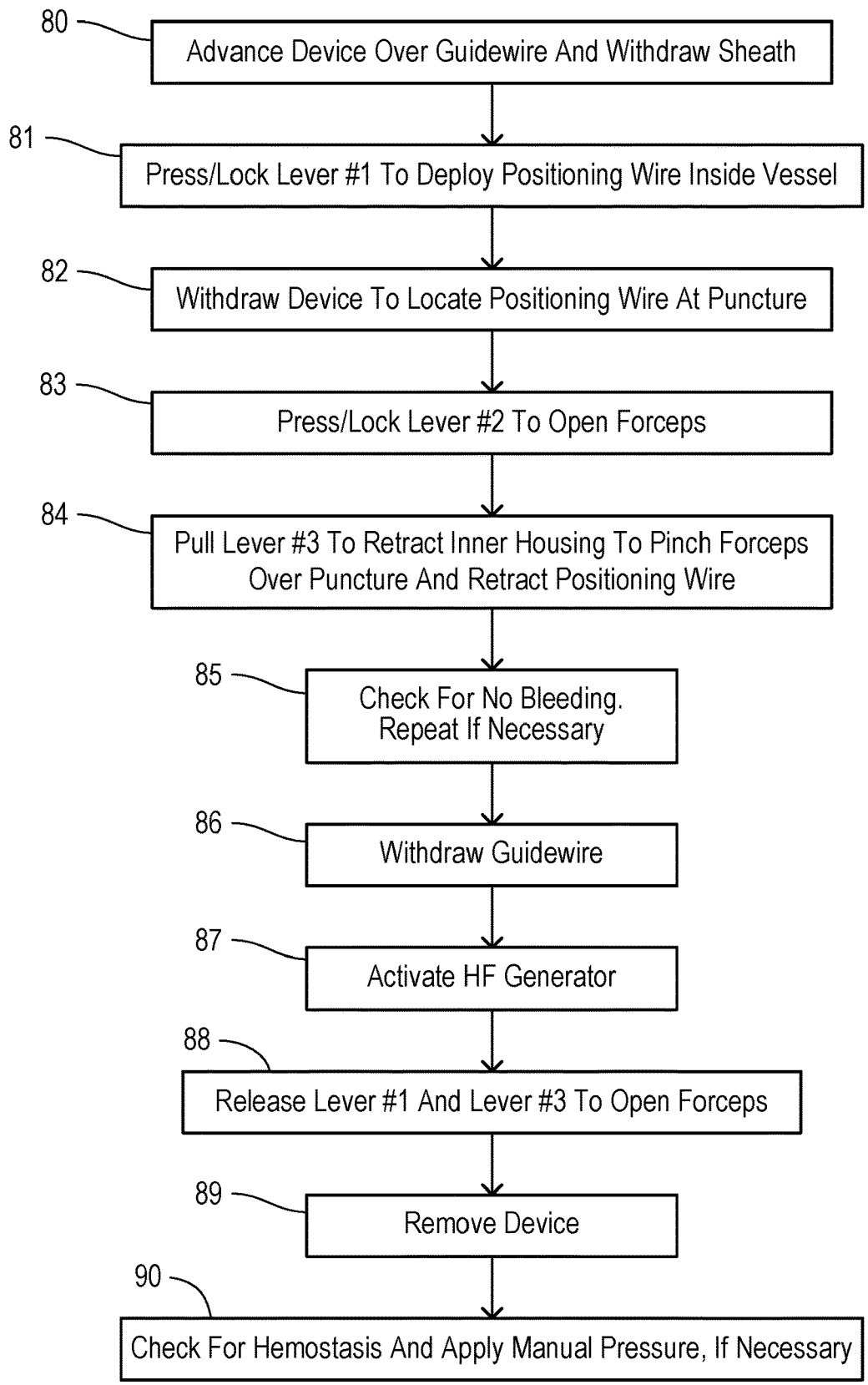
FIG. 19 is a flowchart showing one embodiment of a preferred method of the invention.

A preferred method of the invention is summarized in FIG. 19. Instruments and devices related to an intervention would first be removed from the guidewire so that only the guidewire and the introduced sheath remain. In step 80, the device is advanced over the guidewire so that the forceps and inner tube approach the puncture. The introducer sheath is withdrawn, and it may remain over the distal shaft of the device where it will not interfere with the closing of the puncture. In step 81, the first (positioning) lever for the positioning wire is advanced (e.g., pressed) in a distal direction and then locked in order to deploy the positioning wire inside the blood vessel (as shown in FIG. 10). Consequently, the expanded shape of the distal ends of the positioning wire is deployed on the inside of the blood vessel. In step 82, the device is partially or slightly withdrawn in order to locate the positioning wire at the puncture (as shown in FIGS. 14 and 15) in order to accurately position the puncture site, align the location of the blood vessel with the area to be grasped by the forceps, and to provide a reaction surface for the forceps to push against as they grasp the vessel walls. Preferably, the radial handles of the inner housing lever handles extend parallel (i.e., radially coplanar) to the pivot plane in order to assist the user in orienting the forceps along the lengthwise direction of the vessel (which simultaneously orients the maximum length of the deployed positioning wires in a transverse direction).

With the positioning wires and puncture properly oriented, the forceps lever is advanced (as shown in FIG. 16) by pressing in the distal direction and locking the forceps lever so that the forceps jaws are in an open position (as shown in FIG. 17). In step 84, the radial handles of the inner housing lever are pulled in a proximal direction (as shown in FIG. 18) so that the inner housing retracts to the proximal position, resulting in the forceps jaws pinching together opposing sides of the vessel wall from opposite sides of the puncture, and simultaneously retracting the positioning wires. If successful, the pinched vessel walls will temporarily close the puncture and bleeding will cease. In step 85, the user may check for any bleeding. If bleeding is present, then each of the levers may be restored to their biased positions and steps 82-85 may be repeated until the bleeding has been sufficiently stopped. Then the guidewire is withdrawn in step 86 and the HF generator is activated in step 87.

The HF generator utilizes known techniques in order to apply an appropriate bipolar current magnitude and duration that successfully denatures and seals the vessel around the puncture. Then the inner housing lever and the positioning wire lever are released in step 88, resulting in opening of the forceps jaws while the positioning wire remains in the retracted position. Then the device can be removed in step 89. In step 90, a further check may be performed to determine whether hemostasis has been achieved. If there is any residual bleeding than manual pressure can be applied until hemostasis is achieved.

What is claimed is:

1. A device for closing a puncture in a blood vessel, comprising:
   a housing with a distal shaft and a proximal casing oriented along a longitudinal axis, wherein the housing defines a longitudinal passage to receive a guidewire, wherein the device is configured to be positioned along the guidewire to approach the puncture;
   an inner housing in an internal chamber of the proximal casing, wherein the inner housing is slidable along the longitudinal axis between a distal position and a proximal position, and wherein the inner housing is biased into the distal position;
   a forceps mounted at a distal end of the distal shaft comprising first and second jaws, wherein the first and second jaws are electrically conductive and are electrically insulated from each other, wherein the first and second jaws are configured to be pivoted between an open position and a closed position for grasping the blood vessel around the puncture to be closed, each of the first and second jaws extending across and bisecting the longitudinal axis when in the open position;
   first and second electrical conductors having distal ends connected to the first and second jaws, respectively, and having proximal ends configured to receive a bipolar electrical current;
   a positioning wire retained by the distal shaft and selectably extendable from a retracted position contained in the distal shaft to an extended position with a distal end protruding from the distal shaft beyond the forceps, wherein the protruding distal end is comprised of a shape memory material that reconfigures from a substantially straight shape when stored in the retracted position into a lateral profile extending transverse to the longitudinal axis when in the extended position;
   a positioning lever mounted inside the inner housing and coupled to the positioning wire, wherein the positioning lever is configured to be moved between a first position that places the positioning wire in the retracted position and a second position that places the positioning wire in the extended position, and wherein the positioning lever is biased to the first position; and
   a forceps lever mounted to the inner housing and coupled to the first and second jaws, wherein the forceps lever is configured to be moved between a first position that places the first and second jaws in the closed position and a second position that places the first and second jaws in the open position, and wherein the forceps lever is biased to the first position;
   wherein the inner housing is configured to be moved from the distal position to the proximal position to cause the positioning wire to retract into the distal shaft and the first and second jaws to pivot to the closed position grasping the blood vessel across the puncture so that the puncture can be closed by activating the bipolar electrical current.

2. The device of claim 1 wherein a plurality of radial handles extend in parallel with a pivot plane.

3. The device of claim 1 wherein the lateral profile of the extended positioning wire has a maximum length perpendicular to a pivot plane and a minimum length parallel to the pivot plane.

4. The device of claim 1 further comprising an inner tube mounted in the distal shaft with a lumen configured to receive the guidewire and the positioning wire, wherein the guidewire and positioning wire are independently slidable through the lumen.

5. The device of claim 4 wherein the first and second jaws include a groove for receiving the inner tube when the first and second jaws are in the closed position.

6. The device of claim 1 wherein the inner housing includes first and second tubular chambers for slidably receiving the positioning lever and the forceps lever, respectively.

7. The device of claim 6 further comprising first and second bias springs disposed in the first and second tubular chambers for biasing the positioning lever and the forceps lever to the first positions, respectively.

8. The device of claim 6 wherein the positioning wire is affixed to the positioning lever.

9. The device of claim 8 wherein the positioning lever comprises a positioning radial handle that projects through a guide slot in the inner housing, wherein the guide slot has a longitudinal section to allow longitudinal movement of the positioning lever and a circumferential section forming a first locking feature.

10. The device of claim 6 wherein the forceps lever comprises a pin extending longitudinally to be received in respective slanted slots in the first and second jaws, whereby the first and second jaws pivot in response to a longitudinal position of the forceps lever.

11. The device of claim 10 wherein the forceps lever comprises a forceps radial handle that projects through a guide slot in the inner housing, wherein the guide slot has a longitudinal section to allow longitudinal movement of the forceps lever and a circumferential section forming a second locking feature.

12. The device of claim 1 wherein the positioning wire is comprised of at least two wire members configured to be moved in tandem, wherein the wire members include a first member and a second member that deploy in radially opposite directions to establish a maximum length, wherein the first member and the second member each have a quasi-spiral shape which proceeds radially outward and then bends back in to extend radially inward, wherein portions of the first member and the second member adapted to make contact with the blood vessel are rotated by 90° from the first and second jaws.

13. A method of using a closure device, wherein the closure device includes a housing, an inner housing, a forceps, first and second electrical conductors, a positioning wire, a positioning lever, and a forceps lever, wherein the housing has a distal shaft and a proximal casing oriented along a longitudinal axis, wherein the housing defines a longitudinal passage to receive a guidewire, wherein the inner housing is disposed in an internal chamber of the proximal casing, wherein the inner housing is slidable along the longitudinal axis between a distal position and a proximal position, wherein the inner housing is biased into the distal position, wherein the forceps is mounted at a distal end of the distal shaft and comprises first and second jaws, wherein the first and second jaws are electrically conductive and are electrically insulated from each other, wherein the first and second jaws are configured to be pivoted between an open position and a closed position for grasping a blood vessel around a puncture to be closed, each of the first and second jaws extending across and bisecting the longitudinal axis when in the open position, wherein the first and second electrical conductors have distal ends connected to the first and second jaws, respectively, and have proximal ends configured to receive a bipolar electrical current, wherein the positioning wire is retained by the distal shaft and is selectably extendable from a retracted position contained in the distal shaft to an extended position with a distal end protruding from the distal shaft beyond the forceps, wherein the protruding distal end is comprised of a shape memory material that reconfigures from a substantially straight shape when stored in the retracted position into a lateral profile extending transverse to the longitudinal axis when in the extended position, wherein the positioning lever is mounted inside the inner housing and is coupled to the positioning wire, wherein the positioning lever is configured to be moved between a first position that places the positioning wire in the retracted position and a second position that places the positioning wire in the extended position, wherein the positioning lever is biased to the first position, wherein the forceps lever is mounted to the inner housing and is coupled to the first and second jaws, wherein the forceps lever is configured to be moved between a first position that places the first and second jaws in the closed position and a second position that places the first and second jaws in the open position, and wherein the forceps lever is biased to the first position, the method comprising:

A) advancing the closure device along the guidewire to approach the puncture;

B) advancing the positioning lever from the first position and locking the positioning lever in the second position to place the distal end of the positioning wire inside the blood vessel with the distal end of the positioning wire extended to the lateral profile;

C) partially withdrawing the closure device along the guidewire so that the distal end of the positioning wire centers the puncture with respect to the forceps;

D) advancing the forceps lever from the first position and locking the forceps lever in the second position to pivot the first and second jaws into the open position spanning the puncture;

E) positioning a plurality of radial handles at a predetermined orientation with respect to an axial direction of the blood vessel so that a pivot plane of the first and second jaws is aligned with the axial direction of the blood vessel and so that a maximum length of the lateral profile is perpendicular to the axial direction of the blood vessel;

F) withdrawing the inner housing from the distal position to the proximal position to cause the positioning wire to retract into the distal shaft and the first and second jaws to pivot to the closed position grasping the blood vessel across the puncture; and G) activating the bipolar electrical current to thermally heat the blood vessel grasped between the first and second jaws.

14. The method of claim 13 further comprising the step of withdrawing the guidewire from the closure device between step F and step G.

15. The method of claim 13 further comprising the steps of:

H) unlocking and withdrawing the positioning lever to the first position; and

I) advancing the inner housing from the proximal position to the distal position to cause the first and second jaws to pivot to the open position.

16. A device for closing a puncture in a blood vessel, comprising:

a housing with a distal shaft and a proximal casing oriented along a longitudinal axis, wherein the housing defines a longitudinal passage to receive a guidewire, wherein the device is configured to be positioned along the guidewire to approach the puncture;

an inner housing in an internal chamber of the proximal casing, wherein the inner housing is slidable along the longitudinal axis between a distal position and a proximal position, and wherein the inner housing is biased into the distal position;

a forceps mounted at a distal end of the distal shaft comprising first and second jaws, wherein the first and second jaws are electrically conductive and are electrically insulated from each other, wherein the first and second jaws are configured to be pivoted between an open position and a closed position for grasping the blood vessel around the puncture to be closed, each of the first and second jaws extending across and bisecting the longitudinal axis when in the open position;

first and second electrical conductors having distal ends connected to the first and second jaws, respectively, and having proximal ends configured to receive a bipolar electrical current;

a positioning wire retained by the distal shaft and selectably extendable from a retracted position contained in the distal shaft to an extended position with a distal end protruding from the distal shaft beyond the forceps, wherein the protruding distal end is comprised of a shape memory material that reconfigures from a substantially straight shape when stored in the retracted position into a lateral profile extending transverse to the longitudinal axis when in the extended position;
a positioning lever mounted inside the inner housing and coupled to the positioning wire, wherein the positioning lever is configured to be moved between a first position that places the positioning wire in the retracted position and a second position that places the positioning wire in the extended position, and wherein the positioning lever is biased to the first position; and
a forceps lever mounted to the inner housing and coupled to the first and second jaws, wherein the forceps lever is configured to be moved between a first position that places the first and second jaws in the closed position and a second position that places the first and second jaws in the open position, and wherein the forceps lever is biased to the first position;
wherein the inner housing is configured to be moved from the distal position to the proximal position to cause the positioning wire to retract into the distal shaft and the first and second jaws to pivot to the closed position grasping the blood vessel across the puncture so that the puncture can be closed by activating the bipolar electrical current;
wherein the first and second jaws are configured to be pivoted in a pivot plane, and wherein the lateral profile of the extended positioning wire has a maximum length perpendicular to the pivot plane and a minimum length parallel to the pivot plane.

17. The device of claim 16 wherein the inner housing includes a plurality of radial handles that extend through a plurality of longitudinal guide slots in the proximal casing, and wherein the plurality of radial handles extend in parallel with the pivot plane.

18. The device of claim 16 wherein the positioning wire is comprised of at least two wire members configured to be moved in tandem, and wherein the wire members include a first member and a second member that deploy in radially opposite directions to establish the maximum length.

19. The device of claim 18 wherein the first member and the second member each has a quasi-spiral shape which proceeds radially outward and then bends back in to extend radially inward, wherein portions of the first member and the second member adapted to make contact with the blood vessel are rotated by 90° from the first and second jaws.

20. A method of using a closure device, wherein the closure device includes a housing, an inner housing, a forceps, first and second electrical conductors, a positioning wire, a positioning lever, and a forceps lever, wherein the housing has a distal shaft and a proximal casing oriented along a longitudinal axis, wherein the housing defines a longitudinal passage to receive a guidewire, wherein the inner housing is disposed in an internal chamber of the proximal casing, wherein the inner housing is slidable along the longitudinal axis between a distal position and a proximal position, wherein the inner housing is biased into the distal position, wherein the forceps is mounted at a distal end of the distal shaft and comprises first and second jaws, wherein the first and second jaws are electrically conductive and are electrically insulated from each other, wherein the first and second jaws are configured to be pivoted between an open position and a closed position for grasping a blood vessel around a puncture to be closed, each of the first and second jaws extending across and bisecting the longitudinal axis when in the open position, wherein the first and second electrical conductors have distal ends connected to the first and second jaws, respectively, and have proximal ends configured to receive a bipolar electrical current, wherein the positioning wire is retained by the distal shaft and is selectably extendable from a retracted position contained in the distal shaft to an extended position with a distal end protruding from the distal shaft beyond the forceps, wherein the protruding distal end is comprised of a shape memory material that reconfigures from a substantially straight shape when stored in the retracted position into a lateral profile extending transverse to the longitudinal axis when in the extended position, wherein the positioning lever is mounted inside the inner housing and is coupled to the positioning wire, wherein the positioning lever is configured to be moved between a first position that places the positioning wire in the retracted position and a second position that places the positioning wire in the extended position, wherein the positioning lever is biased to the first position, wherein the forceps lever is mounted to the inner housing and is coupled to the first and second jaws, wherein the forceps lever is configured to be moved between a first position that places the first and second jaws in the closed position and a second position that places the first and second jaws in the open position, wherein the forceps lever is biased to the first position, wherein the first and second jaws are configured to be pivoted in a pivot plane, wherein the inner housing includes a plurality of radial handles that extend through longitudinal guide slots in the proximal casing with a predetermined orientation with respect to the pivot plane, and wherein the lateral profile of the extended positioning wire has a maximum length perpendicular to the pivot plane and a minimum length parallel to the pivot plane, the method comprising the steps of:

A) advancing the closure device along the guidewire to approach the puncture;
B) advancing the positioning lever from the first position and locking the positioning lever in the second position to place the distal end of the positioning wire inside the blood vessel with the distal end of the positioning wire extended to the lateral profile;
C) partially withdrawing the closure device along the guidewire so that the distal end of the positioning wire centers the puncture with respect to the forceps;
D) advancing the forceps lever from the first position and locking the forceps lever in the second position to pivot the first and second jaws into the open position spanning the puncture;
E) positioning the plurality of radial handles at a predetermined orientation with respect to an axial direction of the blood vessel, wherein the positioning of the plurality of radial handles at the predetermined orientation orients the maximum length of the lateral profile of the positioning wire perpendicularly with respect to the axial direction of the blood vessel;
F) withdrawing the inner housing from the distal position to the proximal position to cause the positioning wire to retract into the distal shaft and the first and second jaws to pivot to the closed position grasping the blood vessel across the puncture; and
G) activating the bipolar electrical current to thermally heat the blood vessel grasped between the first and second jaws.

* * * * *